(12) United States Patent
Nakao

(10) Patent No.: US 7,396,329 B2
(45) Date of Patent: *Jul. 8, 2008

(54) ENDOSCOPIC RETRACTOR INSTRUMENT AND ASSOCIATED METHOD

(75) Inventor: Naomi L. Nakao, New York, NY (US)

(73) Assignee: Granit Medical Innovations, LLC, New York, NY (US)

( * ) Notice: Subject to any disclaimer, the term of this patent is extended or adjusted under 35 U.S.C. 154(b) by 456 days.

This patent is subject to a terminal disclaimer.

(21) Appl. No.: 10/414,806

(22) Filed: Apr. 16, 2003

(65) Prior Publication Data

US 2003/0225433 A1    Dec. 4, 2003

Related U.S. Application Data

(63) Continuation-in-part of application No. 09/978,413, filed on Oct. 16, 2001, now Pat. No. 6,913,610.

(51) Int. Cl.
A61B 1/32  (2006.01)

(52) U.S. Cl. ..................... 600/204; 606/192

(58) Field of Classification Search ......... 606/110–111, 606/114–115, 192–194; 604/101.01, 96.01, 604/101.03–101.05, 96; 600/204, 207, 208; 623/1, 25

See application file for complete search history.

(56) References Cited

U.S. PATENT DOCUMENTS

| | | | | | |
|---|---|---|---|---|---|
| 4,183,102 | A | * | 1/1980 | Guiset | 623/1.25 |
| 4,984,564 | A | * | 1/1991 | Yuen | 600/207 |
| 5,865,728 | A | * | 2/1999 | Moll et al. | 600/204 |
| 6,146,401 | A | * | 11/2000 | Yoon et al. | 606/192 |
| 6,409,723 | B1 | * | 6/2002 | Edwards | 606/41 |
| 6,913,610 | B2 | * | 7/2005 | Nakao | 606/192 |

* cited by examiner

Primary Examiner—Michael J. Hayes
Assistant Examiner—Victor Nguyen
(74) Attorney, Agent, or Firm—R. Neil Sudol; Henry D. Coleman; William J. Sapone

(57) ABSTRACT

An endoscopic retractor is an elongate balloon having an expanded configuration having two end portions and a plurality of struts or spacer members extending between the end portions. The retractor balloon is a single tubular preform bent during manufacture to form the expanded configuration. Thus, the struts or spacer members are integral with both end portions and define therewith a single flow path for inflation or pressurization fluid.

19 Claims, 4 Drawing Sheets

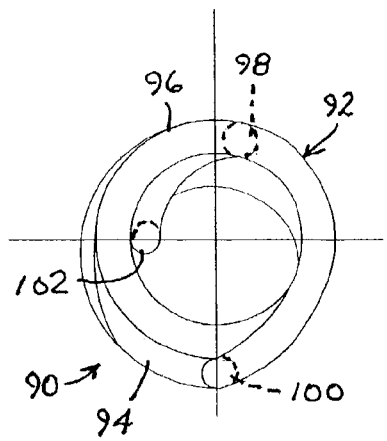
FIG. 6
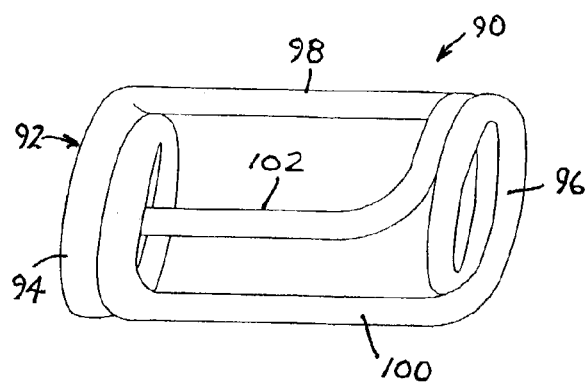
FIG. 7
FIG. 5
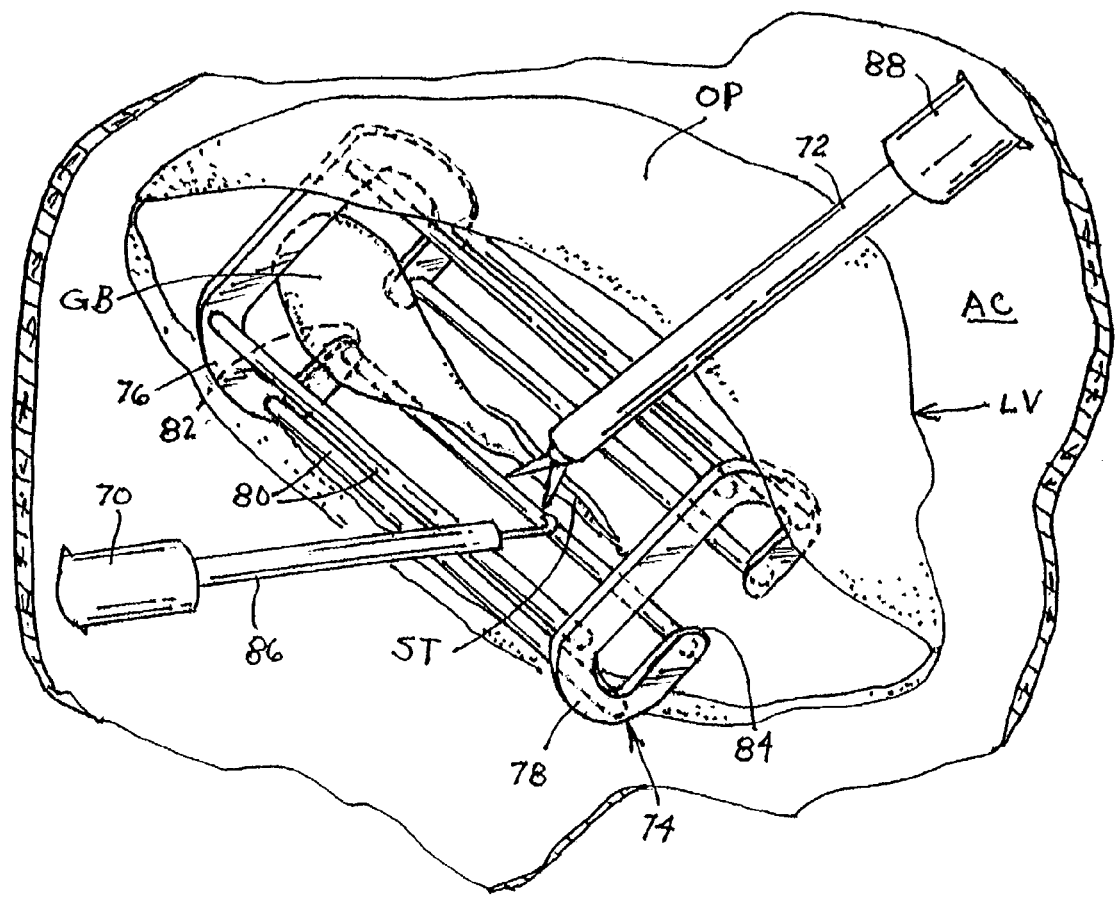

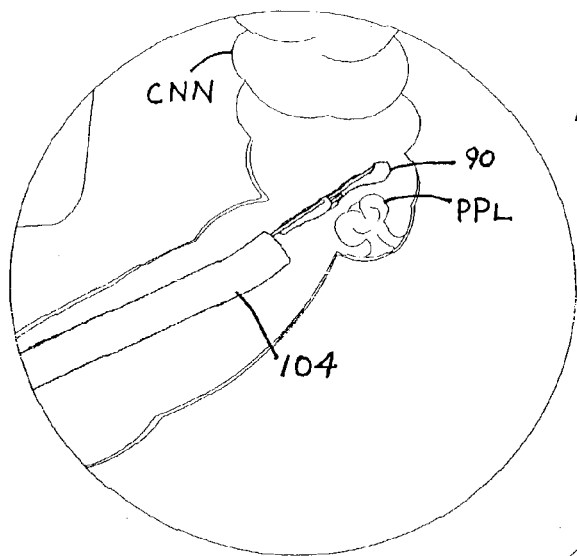
FIG. 8A
FIG. 8B
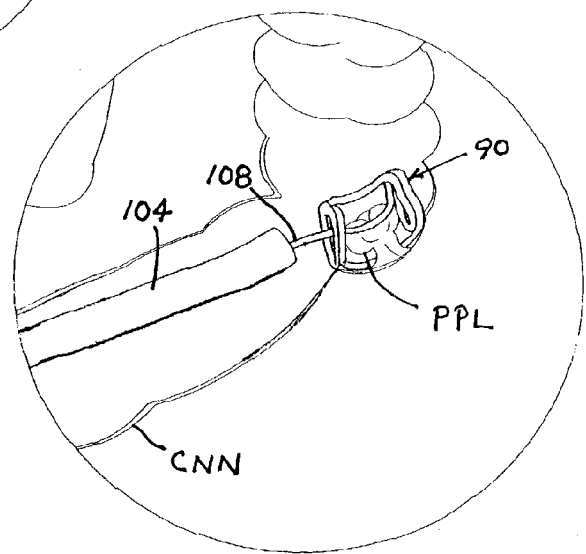
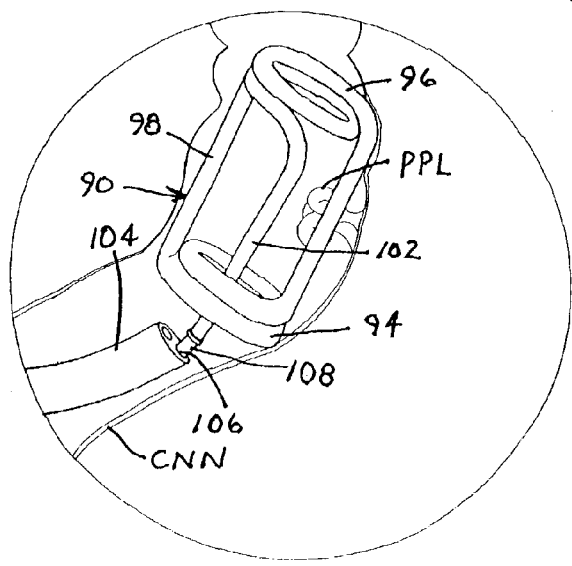
FIG. 8C

ENDOSCOPIC RETRACTOR INSTRUMENT AND ASSOCIATED METHOD

CROSS-REFERENCE TO RELATED APPLICATION

This application is a continuation-in-part of application Ser. No. 09/978,413 filed Oct. 16, 2001 now U.S. Pat. No. 6,913,610.

BACKGROUND OF THE INVENTION

This invention relates to a medical device and to an associated medical technique. More particularly, this invention relates to an endoscopic instrument and to an endoscopic method.

Flexible endoscopes are inserted into the digestive tract for diagnostic and therapeutic purposes. Endoscopes generally include a light guide for transmitting optical-wavelength electromagnetic radiation into the patient. Images are captured, typically via lenses and an optical fiber bundle or a charge-coupled device, whereby a user can visually inspect the inner walls or surfaces of the digestive tract. One common objective of endoscopic investigations in the digestive tract is to detect the presence of polyps. Where a polyp is visually detected, particularly in the colon, it should be severed, captured, and removed from the patient. Alternatively, particularly where the polyp may be a malignant cancer, the polyp may be severed and captured for extraction from the patient.

One problem frequently encountered by endoscopists is that folds of tissues in the digestive tract and particularly the colon can obscure polyps so that they can be overlooked. The colon is often collapsed and may be partially or completely draped over a lesion. In order to distend the walls of the colon, the endoscopist often pumps air into the organ. However, if too much air is introduced, the colon could perforate. Also, the patient is made quite uncomfortable with introduction of substantial amounts of air.

Another problem with visualization during an endoscopic procedure is that polyps sometimes bleed when they are severed. If the lesion site cannot be adequately visualized, it is difficult to contain and control the bleeding.

OBJECTS OF THE INVENTION

It is a general object of the present invention to provide a retractor instrument utilizable in surgical or diagnostic procedures.

A more specific object of the present invention is to provide such an instrument assembly which is utilizable in endoscopic procedures.

A further object of the present invention is to provide such an instrument assembly which is inexpensive and/or easy to use.

It is an even more specific object of the present invention to provide an endoscopic instrument assembly which is particularly suitable for use with flexible endoscopes during investigations of the digestive or gastro-intestinal tract.

It is another object of the present invention to provide an endoscopic procedure for facilitating visual inspection of the digestive tract and other internal body cavities.

An additional object of the present invention is to provide an instrument and/or method for use with flexible endoscopes, which reduces patient discomfort and risk by potentially reducing the amount of air introduced into the gastrointestinal tract.

It is yet another object of the present invention to provide an endoscopic instrument that is disposable.

These and other objects of the invention will be apparent from the drawings and descriptions herein. Although every object of the invention is attained by at least one embodiment of the invention, there is not necessarily any one embodiment that achieves all of the objects of the invention.

SUMMARY OF THE INVENTION

A medical instrument comprises, in accordance with the present invention, a retractor in the form of an expandable balloon and a connector element for attaching the balloon at least indirectly to an endoscopic instrument so that an expanded configuration the balloon retracts tissues located ahead of a distal tip of the endoscopic instrument to facilitate visualization.

The connector element may include a tubular member insertable through a biopsy channel of the endoscopic instrument. The balloon is preferably a single tubular member bent to assume an at least partially coiled form.

An endoscopic retractor comprises, in accordance with a preferred embodiment of the present invention, an elongate balloon having an expanded configuration having two end portions and a plurality of struts or spacer members extending between the end portions. The retractor balloon is a single tubular preform bent during manufacture to form the expanded configuration. Thus, the struts or spacer members are integral with both end portions and define therewith a single flow path for inflation or pressurization fluid. Simplicity and ease of manufacture is a key advantage of this preferred embodiment.

Pursuant to another feature of the present invention, the balloon is provided with means for operatively attaching the balloon to an endoscopic insertion member. The attachment means may comprise a catheter extending through a biopsy channel of the endoscope insertion member, the catheter serving in part as a pusher for ejecting the balloon in its collapsed configuration from the biopsy channel of the endoscope and in part as a conduit for guiding a pressurization fluid (liquid, gas) to the balloon upon ejection thereof from the endoscope. The catheter and the collapsed balloon retractor may be stored at least partially inside an outer tube removably inserted in the biopsy channel of the endoscope.

Preferably, at least one of the end portions of the retractor balloon takes the form of a tightly wound spiral or coil. The coil has more than one turn, with successive turns being possibly bonded (e.g., glued) to one another to ensure that the coil assumes a predetermined shape upon an inflation or expansion of the balloon.

The struts or spacer members preferably extend substantially parallel to one another. They may extend parallel to an axis of the expanded configuration.

More generally, an endoscopic retractor instrument assembly comprises, in accordance with the present invention, a balloon or bladder having a pair of expandable or inflatable end portions and at least one expandable or inflatable spacer portion connecting the end portions to one another. An inflation component is operatively coupled with the balloon or bladder for inflating the balloon or bladder from the collapsed configuration to an expanded use configuration in which the spacer portion pushes the end portions apart from one another.

In a particular embodiment of the invention, at least one end portion of the balloon or bladder takes the form of a coil. The coil is a tightly wound spiral. The spacer portion is preferably one of a plurality of elongate tubes extending between and communicating with each of the end portions.

As discussed above, the retractor balloon is preferably manufactured from a single elongate preform which is differentially bent and provided with a "memory" to form the end portions and spacer portions.

An endoscopic retractor instrument comprises, in accordance with another embodiment of the invention, a plurality of parts movably connected to one another, a fastening component for mounting the parts in a collapsed or reduced-size configuration to a distal end portion of an insertion member of an endoscope, and an actuator operatively connected to the parts for enabling a movement of the parts relative to one another so that the parts assume an enlarged or expanded configuration extending at least partially in a distal direction away from the distal end portion of the insertion member for spreading internal tissues of a patient to facilitate a visualization of the tissues via the endoscope.

An endoscopic retractor instrument assembly comprises, in accordance with another particular embodiment of the present invention, an insertion or deployment tube insertable into a biopsy channel of an endoscope, a balloon or bladder having a pair of expandable or inflatable end portions and at least one expandable or inflatable spacer portion connecting the end portions to one another, the balloon or bladder being disposed in a collapsed configuration inside the tube. An inflation element is operatively coupled with the balloon or bladder for inflating the balloon or bladder from the collapsed configuration to an expanded use configuration in which the spacer portion pushes the end portions apart from one another.

Naturally, a retractor balloon or bladder in accordance with the invention expands radially or transversely, as well as longitudinally or axially. The transverse expansion of the instrument enables the application of pressure to the colon wall or other portion of a digestive tract or internal body tissues to separate the tissues and smooth out folds. This facilitates inspection and the performance of endoscopic operations on target tissues inside the patient.

The inflation element of a retractor instrument assembly in accordance with the present invention may include a feed tube or conduit connected to the balloon or bladder for enabling the delivery of a pressurizing fluid such as saline solution or a gas (air) to the balloon or bladder. This inflation tube is typically a flexible line extending back along an endoscopic insertion member to a pressurization device (e.g., a syringe) outside of the patient. The inflation tube may extend through the biopsy channel of the endoscope.

The inflation element of a retractor instrument assembly in accordance with the present invention may further include a one-way valve disposed between the inflation tube and the balloon or bladder. The valve automatically prevents the escape of the pressurizing fluid from the balloon or bladder and thus facilitates the use of the instrument in an endoscopic procedure. The valve may be disposed inside the balloon or bladder or alternatively in a nipple or nub element connected thereto. Where the inflation tube extends through an endoscopic biopsy channel, the tube may be removably connected to the balloon or nipple, for instance, via a screw connection or a frangible link. The extraction of the inflation tube upon the disconnection thereof from the balloon clears the site of interest and thereby facilitates the performance of additional diagnostic or therapeutic procedures via the biopsy channel. This removal is not necessary where a sheath having multiple channels is used.

In a form of an endoscopic retractor instrument assembly having a pair of expandable or inflatable end portions and at least one expandable or inflatable spacer portion connecting the end portions, the inflatable end portions are toroidal or ring-shaped. In addition, the spacer portion is one of a plurality of elongate expandable or inflatable spacer portions each having one end connected to and communicating with one of the end portions and an opposite end connected to and communicating with another one of the end portions. Moreover, at least one of the elongate spacer portions may be provided with a semi-rigid stiffener rod which facilitates ejection of the balloon or bladder from the distal end of the insertion or deployment tube by a pusher rod.

An endoscopic retractor instrument assembly comprises, in accordance with a more general description of the present invention, (a) a plurality of parts movably connected to one another, (b) componentry for mounting the parts in a collapsed or reduced-size configuration to a flexible and steerable insertion member of an endoscope, and (c) one or more actuation elements operatively connected to the parts for enabling a movement of the parts relative to one another so that the parts assume an enlarged or expanded configuration for spreading internal tissues of a patient.

The relatively movable parts of the endoscopic retractor instrument assembly may include, as discussed above, a plurality of expandable or inflatable balloon or bladder parts.

A medical method in accordance with another embodiment of the present invention utilizes an endoscopic retractor instrument and a flexible endoscope having an insertion member. The method comprises (i) inserting a distal end portion of the insertion member into a patient, (ii) deploying the retractor instrument from the distal end portion of the insertion member upon inserting of the distal end portion into the patient, and (iii) thereafter operating the retractor instrument to engage an inner wall of an internal organ of the patient so as to spread the inner wall.

Where the retractor instrument includes a plurality of parts movably connected to one another and where the retractor instrument is attached to an outer surface of the insertion member during the inserting of the distal end portion into the patient, the operating of the retractor instrument includes moving the parts relative to one another to increase an effective diameter of the retractor instrument. Where the internal organ is tubular such as the colon, so that the inner wall is roughly cylindrical, the expanding of the retractor instrument enables a stretching of the organ to remove folds from the inner wall. This facilitates a rigorous visual inspection of the internal organ, as well as any endoscopic surgical procedures on the tissues of the organ.

Where the retractor instrument includes a plurality of prongs arranged in a cylindrical configuration on a ring member surrounding the insertion member during the inserting of the distal end portion into the patient, the operating of the retractor instrument including spreading the prongs so that the retractor instrument assumes a substantially conical configuration.

Where the retractor instrument includes a balloon or bladder member, the operating of the retractor member includes feeding a fluid to the balloon or bladder to inflate the balloon or bladder from a collapsed configuration to an expanded use configuration. Then the deploying of the retractor instrument includes ejecting the retractor instrument in the collapsed configuration from a tubular member into the patient.

The present invention enables the insertion of a retractor deep inside a patient through a natural body opening. At the site of interest, whether a diagnostic or surgical site, the retractor is expanded to a configuration many times larger than the collapsed insertion configuration, thereby enabling a substantial spreading of internal tissues.

A retractor pursuant to at least one embodiment of the present invention may remain by itself in the colon or other lumen or generally inside the patient and does not require continued support by or connection to the insertion instrument, whether that instrument is a flexible endoscope, a trocar sleeve or other device. This independent support capability of the particular retractor allows the operating surgeon to use the insertion instrument for the deployment of other surgical tools.

In a retractor pursuant to the present invention, windows or openings are provided which allow direct access to the internal tissues of the patient from the distal end of an endoscopic insertion member. Upon expansion, the retractor provides transverse pressure on the wall of the gastrointestinal tract and expands the organ and smoothens the folds, allowing for the viewing and potential diagnostic and/or interventional activity. The windows or openings defined by the expanded retractor allow for an instrument such as a snare cautery device to capture a polyp. The openings are not so large, however, that the retraction process is impaired.

The inner diameter of a retractor pursuant to the present invention is preferably large enough to allow the operator to comfortably operate on a polyp or other lesion. The outer diameter of the device is sized correctly to support the colon walls in an open position but is not so large as to cause colonic perforation. The balloon diameter is large enough to allow support of the colon wall, but small enough as to not obstruct the visibility of the colon being retracted.

A retractor balloon in accordance with the invention is made of a rubber or elastic polymeric material with limited expandability so that it will not be overextended, and burst. The collapsed configuration of the device after its use is flexible enough to permit extraction of the device from the colon or other hollow organ or reintroduction of the device into a sheath with which it was introduced.

Where a retractor balloon in accordance with the present invention is attached to the distal end of an endoscope, the proximal end of the balloon may be configured to fit snugly, or with a clamping or securing attachment, over the outside of the distal end of the endoscope in a deflated configuration. The distal end of the balloon is configured so as not to interfere with insertion of the endoscope or visualization through the endoscope. Thus, the collapsed balloon is situated outside the field of visualization surrounding the endoscope lens, either in the same transverse plane as the lens or proximal to it. The endoscope with the attached retractor in a collapsed configuration is inserted into a hollow organ, e.g., the colon, to the most proximal end (farthest inside the patient) of the hollow organ as determined by the endoscopist. The balloon is then inflated using the inflation element at the proximal end of the insertion tubing. The distal portion of the balloon unfolds during this process and moves distal to the distal end of the endoscope, the proximal portion of the balloon inflates around the endoscope and may further secure the device to the endoscope. The spacer members secure the two balloon ends at a predetermined distance from one another. The endoscopist then slowly retracts the endoscope with the enlarged or expanded retractor and views the GI tract between the two ends of the retractor as the retractor places pressure on and expands or stretches the wall of the GI tract, minimizing tissue folds that can interfere with viewing of the organ. The spacing (windows, openings) between the ends of the balloon allow for diagnostic and interventional procedures by the endoscopist. In other words, as the endoscope is pulled back, the physician performs his or her examination, and the colon collapses behind the enlarged or expanded retractor, which provides a telescoped part of the colon in front of (distal to) the lens that is now distended to its full inner diameter, allowing for visualization of polyps or other pathology behind every fold and 360 degrees around the wall of the colon. When a polyp happens to come into view, the withdrawal procedure is interrupted, the telescope (retractor) is situated framing the polyp, and removal of the polyp takes place. Then, the polyp is captured and with the retractor still in place the withdrawal continues and the rest of the colon or other hollow organ is visualized.

BRIEF DESCRIPTION OF THE DRAWINGS

FIG. 5 is a schematic perspective view of a modified balloon or bladder retractor, showing the balloon or bladder retractor in an inflated use configuration inside an abdominal cavity, retracting a liver away from a gall bladder during performance of a laparoscopic cholecystectomy.

FIGS. 6 and 7 are an end elevational view and a side elevational view, on an enlarged scale, of another balloon-type endoscopic retractor in accordance with the present invention.

FIGS. 8A-8F are schematic cross-sectional views of a human colon, showing successive steps in the utilization of the balloon-type endoscopic retractor of FIGS. 6 and 7 to perform an endoscopic polypectomy.

DETAILED DESCRIPTION OF THE PREFERRED EMBODIMENTS

Figure 1:
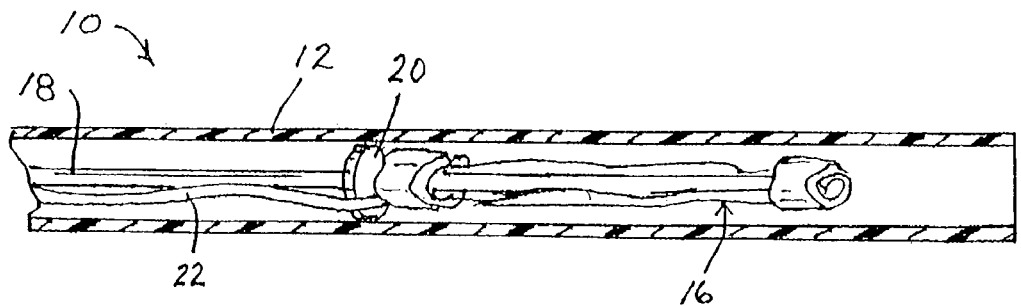
FIG. 1 is a schematic longitudinal cross-sectional view of an endoscopic retractor instrument assembly in accordance with the present invention, showing a balloon or bladder member in a collapsed insertion configuration.
Figure 2:
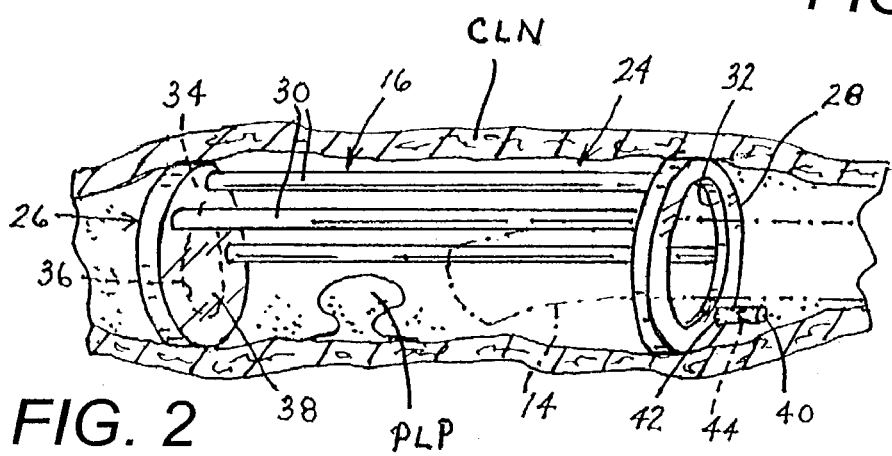
FIG. 2 is a schematic perspective view of the balloon or bladder member of FIG. 1, showing the balloon or bladder in an inflated use configuration inside a colon.

As illustrated in FIG. 1, an endoscopic retractor instrument assembly 10 comprises an insertion or deployment tube 12 insertable into a biopsy channel (not shown) of an endoscope insertion member 14 (see FIG. 2). The assembly 10 additionally comprises a balloon or bladder 16 disposed in a collapsed configuration inside a distal end portion (not separately designated) of the insertion or deployment tube 12. A pusher rod 18 extending through tube 12 is formed at a distal end with a flange 20 engageable with a proximal end of the collapsed balloon 16. To eject the collapsed balloon 16 from the distal end of tube 12, pusher rod 18 is shifted in the distal direction (away from the user).

The retractor assembly 10 further comprises a flexible conduit or tubule 22 extending through tube 12 to balloon 16. Conduit or tubule 22 is connected at a distal end to balloon 16 and communicates therewith to enable channeling of a pressurization fluid, e.g., a saline solution or a gas such as air, to the balloon for purposes of inflating the balloon. At a proximal end, tubular 22 is connected to a source of the pressurization fluid, such as a syringe (not shown) or canister of carbon dioxide (not shown).

During an endoscopic operation, a distal end portion of endoscope insertion member 14 is inserted into a patient, for instance, into the colon CLN (FIG. 2) of the patient. After the distal end of endoscope insertion member 14 attains a selected location or site inside the bowel or colon CLN, as determined, for instance, through a visual inspection of the bowel wall using the optical componentry of the endoscope, insertion or deployment tube 12 is shifted distally through the biopsy channel (not shown) of the endoscope so that a distal end of tube 12 extends into colon CLN. At that juncture, rod 18 is shifted in the distal direction relative to tube 12 to eject balloon 12 into colon CLN. At that point in the procedure, the balloon 16 is still in its collapsed or deflated insertion configuration. Pressurization fluid is then fed to the collapsed balloon 16 via conduit or guide tubule 22 to inflate the balloon from the collapsed configuration to an expanded use configuration 24 shown in FIG. 2.

As shown in FIG. 2, balloon 16 has a pair of expandable or inflatable end members 26 and 28 and a plurality of expandable or inflatable spacer rods 30 connecting the end members to one another. Spacer rods 30 connect the end members 26 and 28 to one another so that the end members and the spacer rods are parts of the same unitary balloon structure 16 and so that the end members communicate with one another via the spacer member. In the inflated or expanded configuration of balloon 16, rods 30 push end members 26 and 28 away from one another, thus generating a retractor action tending to longitudinally spread tissues of the inner wall of colon CLN. In addition, end members 26 and 28 are expanded in a transverse direction so as to come into a frictional or clamping contact with the inner surface of the colon CLN.

Spacer rods 30 are disposed along one side of the retractor balloon or bladder 16. An opposing side (lower side in FIG. 2) is thus left open and unobstructed to facilitate an approach of the distal end of endoscope insertion member 14 to a polyp PLP or other site of interest along the inner wall of colon CLN. In general, spacer rods 30 are disposed so as not only to spread and hold end members 26 and 28 away from one another but also to facilitate the performance of an endoscopic diagnostic investigation or surgical operation on stretched and exposed organic tissues in the spaces between the rods. The surgeon is provided with sufficient room to work without the retractor obstructing the field.

End members 26 and 28 have a circular configuration adapted to uniformly engage the cylindrical inner surface or lumen of colon CLN. At least one end member 28 has a toroidal or ring shape defining an opening 32 traversed by endoscope insertion member 14, as shown in FIG. 2) after deployment of the retractor balloon 16. In deployment, balloon 16 smooths out folds (not shown) in the inner wall of colon CLN, thus enabling a user access to irregularities such as a polyp PLP. The other end member 26 of balloon 16 preferably has no traversable aperture like opening 32. Instead, where end member 26 is formed as a toroidal body 34 with an aperture 36, that aperture is covered by a membrane or screen 38 (collectively "membrane") for preventing the polyp PLP from rolling away from endoscope insertion member 14 should the polyp be severed from the colon in the course of a snare cauterization operation. Membrane 38 may additionally serve to entrain a severed polyp during a removal of the retractor balloon 16, thus acting as a capture pouch or retrieval device.

Upon the inflation of balloon 16 and prior to the passing of the distal end of endoscope insertion member 14 through opening 32, inflation conduit or tubule 22 may be severed proximately to the expanded balloon, at an end 40 of a nipple or nub element 42. To that end, nipple 42 may be provided at its point of connection to tubule 22 with a frangible section (not separately illustrated) for facilitating the detachment of the tubule. The breaking of the connection may be achieved by twisting tubule 22 or by cutting the frangible section with an endoscopic scissors (not shown) inserted through the endoscope biopsy channel.

Alternatively, tubule 22 may be connected to nipple 42 via any equivalent method, such as a threaded coupling, a force-lock fit, or a snap-on coupling (none separately illustrated). In the case of a threaded or screw coupling, detachment of tubule 22 from nipple 42 is implemented by turning the tubule from the proximal end thereof. Of course, tubule 22 would be made of a material with a sufficient rigidity to transmit the twisting torque from the proximal end outside the patient to the distal end at nipple 42. In the case of a force-lock fit, a separate rod or the distal end of the endoscope may be used to hold the nipple 42 while the tubule 22 is pulled in a proximal direction.

In order to prevent the escape of pressurization fluid from balloon 16 after the detachment of tubule 22, nipple 42 is provided with a one-way valve 44. It is to be noted that valve 44 may be alternatively disposed inside balloon or bladder 16 rather than in nipple 42.

As mentioned above, end members 26 and 28 expand radially or transversely to a longitudinal axis of the balloon 16 and transversely to the colon CLN. In order to enhance the gripping of the colon wall by end members 26 and 28 This transverse expansion of the instrument enables the application of pressure to the colon wall or other portion of a digestive tract to expand the organ and smooth out folds. To facilitate the gripping of the colon wall by end members 26 and 28, those members may be formed with outwardly protruding barbs, nubs, teeth or fingers (not shown).

At least one of the elongate spacer members 30 of retractor balloon or bladder 16 may be provided with a semi-rigid stiffener rod (not shown) which facilitates ejection of the balloon or bladder from the distal end of the insertion or deployment tube 12 by pusher rod 18.

After termination of the diagnostic or treatment procedures carried out via the endoscope, the balloon 16 is at least partially deflated simply by puncturing the balloon with a hot snare, a hot biopsy forceps, an endoscopic scissors or cutting device (not shown). The deflated balloon may be gripped by an endoscopic grasper or biopsy forceps (not shown) and dragged out of the patient with the endoscope insertion member. Where a severed polyp is to be removed with the retractor balloon 16 acting as a capture pouch, it may be desirable to retain a certain degree of pressurization of balloon 16 so that the trailing end member 26 retains some of its expanded form. In that case, limited depressurization of balloon 16 may be achieved by reattachment of tubule 22 to nipple 42 and use of an attached syringe (not shown) to extract a portion of the liquid or gas in balloon 16.

Where a severed polyp is extracted separately, for instance, using a retrieval pouch or snare, it is possible in at least some case to leave the deflated retractor balloon 16 inside the colon for evacuation with the patient's stool in due course subsequent to the endoscopic procedure.

Figure 4:
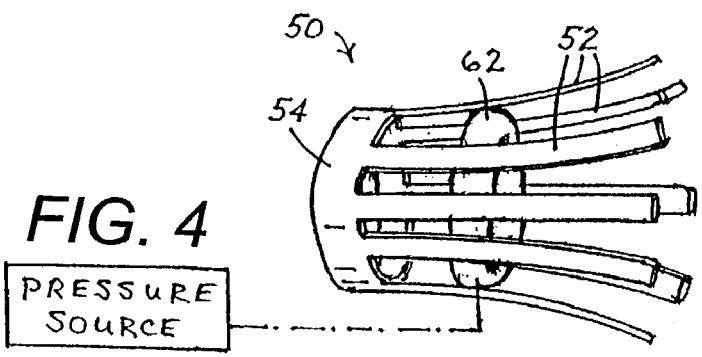
FIG. 4 is a schematic perspective view of the expandable member of FIG. 3, showing that member is an expanded use configuration.
Figure 3:
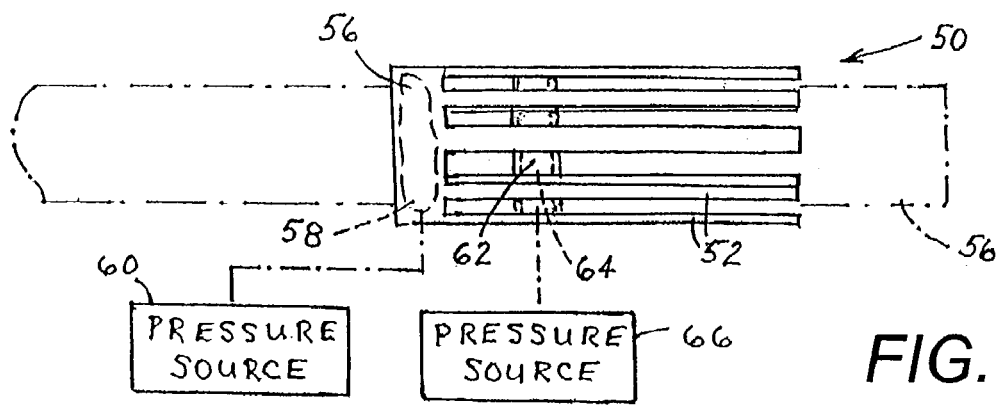
FIG. 3 is a schematic side elevational view of another endoscopic retractor instrument assembly in accordance with the present invention, showing an expandable member in a collapsed insertion configuration.

Another embodiment of a retractor instrument assembly 50 for use in flexible endoscopic investigations is depicted inn FIGS. 3 and 4. Generally, the endoscopic retractor instrument assembly 50 a plurality of prongs or finger parts 52 movably connected to one another via a ring-shaped base 54 made of substantially rigid material such as stainless steel. Prongs 52 normally assume, in the absence of external forces, a straight linear configuration, as shown in FIG. 3, so that the prongs are parallel to one another and disposed in a cylindrical configuration. In this configuration of prongs 52, the retractor assembly may be mounted to an outer surface of a flexible endoscope insertion member 56. Prongs 52 have sufficient flexibility so as the accommodate any bending that endoscope member 56 may undergo during an endoscopic medical procedure.

The endoscope retractor assembly 50 of FIGS. 3 and 4 further includes a toroidal balloon 58 attached to an inner surface of ring-shaped base 54 for enabling a releasable clamping of the retractor assembly to endoscope insertion member 56. To that end, balloon 58 communicates with a pressure source 60 such as a syringe.

Retractor assembly 50 additionally comprises an actuator in the form of a toroidal balloon 62 mounted on an exterior side of a rigid sleeve or collar 64 rigidly fixed to base 54. A pressure source 66 is operatively coupled with balloon 62 for inflating the same to push prongs 52 in a radially outward direction, whereupon the retractor assembly 50 assumes the flared expanded configuration of FIG. 4.

Upon arrival of the distal end of endoscope insertion member 56 at a desired site inside a patient, pressure source 66 is activated to pressurize balloon 62, thereby pressing prongs 52 outwardly to grip the lumen wall of a colon CLN (FIG. 2). At that point, pressure source 60 is operated to deflate balloon 58 from an expanded clamping configuration, thereby enabling a sliding of the endoscope insertion member 56 relative to the retractor assembly 50. The expanding of retractor assembly 50 spreads the walls of the colon and facilitates visual inspection of the colon via the optics of the endoscope.

Enhanced retraction action with the retractor assembly 50 of FIGS. 3 and 4 may be attained by utilizing two such assemblies, One or more rods (not shown) may be provided for spacing the two assemblies at a distance effective to longitudinally spread the tissues of the colon.

If considered necessary by the endoscopist, a flexible sleeve in the form of a cylindrical membrane or film (not shown) may be disposed over retractor assembly 50 and endoscope insertion member 56 during an insertion procedure, to protection the colon. Upon arrival of the distal end of the insertion member 56 at the desired site inside the patient, the sleeve is pulled in the proximal direction to uncover the retractor assembly or assemblies 50.

FIG. 5 depicts an endoscopic retractor 74 in an inflated use configuration in an abdominal cavity AC of a patient. More particularly, retractor 74 is deployed around a gall bladder GB to prop open and separate the surrounding liver LV from the gall bladder. As discussed above with reference to retractor balloon 16 of FIGS. 1 and 2, retractor 74 is an inflatable balloon inserted in a collapsed configuration through an endoscopic device such as a laparoscopic cannula or trocar sleeve 70. As further discussed above with reference to FIGS. 1 and 2, retractor 74 may be disposed in the collapsed configuration inside a distal end portion of an insertion or deployment tube (not shown). The collapsed retractor 74 may be pushed out of the insertion or deployment tube by a pusher rod (not shown) upon a passing of the insertion or deployment tube through cannula 70.

Upon the introduction of the collapsed retractor 74 in abdominal cavity AC, the retractor is manipulated by laparoscopic forceps 72 into a suitable position adjacent to the liver LV in the area of the gall bladder GB. The expansion of retractor 74 from the collapsed configuration to the expanded configuration shown in FIG. 5 is accomplished by the procedures described above.

Retractor 74 has a pair of expandable or inflatable C-shaped end members 76 and 78 and a plurality of expandable or inflatable spacer rods 80 connecting the end members to one another. In the inflated or expanded configuration of balloon retractor 74, rods 80 push end members 76 and 78 away from one another, thus generating a retractor action tending to longitudinally spread tissues of liver LV. In addition, end members 76 and 78 are expanded in a transverse direction so as to push an overhanging portion OP of liver LV away from gall bladder GB. In most procedures, the retractor 74 is inserted in a collapsed or partially inflated condition around bladder GB. Completion of the inflation proceeds thereafter to lift overhanging portion OP up and away from the bladder GB.

End members 76 and 78 are provided with respective slots 82 and 84 because a stump ST of the gall bladder GB is connected to the liver LV. Most of a cholecystectomy procedure is directed to isolating the stump ST, which contains three critical structures, namely, the cystic duct, the cystic artery and the cystic vein (not separately illustrated). Those three structures must be separated and individually clamped and cut prior to a severing of the bladder's stump ST. Slots 82 and 84 enable a deployment of retractor 74 about the gall bladder GB.

End members 76 and 78, as well as end members 26 and 28, do not necessarily have a toroidal or circular configuration. Other geometric forms are possible, including rectangular, triangular, hemispherical, kidney-shaped, etc.

Retractor 74 may remain in abdominal cavity AC during an entire endoscopic procedure, after the retractor has been installed under overhanging liver portion OP, without support by or connection to any cannula 70 or 88. Those cannulas may then be used for the deployment of other laparoscopic instruments such as a cauterization probe or cutting element 86. There is no need to dedicate or relegate a cannula 70 or 88 to the retraction of overhanging liver portion OP. Of course, a connection of balloon retractor 74 to or through a cannula 70 may be retained to facilitate a repositioning of the retractor during the operation.

Retractor 74 may be used for other kinds of operations in rigid endoscopy, such as laparoscopic Nissan Fundoplication and laparoscopic colon resections.

As depicted in FIGS. 6 and 7, another retractor 90 for use in endoscopic procedures (flexible endoscopic, laparoscpic, thoracoscopic, etc.) comprises, in an enlarged or expanded configuration, a balloon or bladder 92 forming a cage having opposed end longitudinally spaced end portions 94 and 96 each in the form of a tightly wound spiral or coil having approximately one-and-a-half windings. End portions 94 and 96 are connected to one another by a pair of substantially diametrically opposed transversely spaced elongate spacer portions 98 and 100. Spacer portion 100 communicates at opposite ends with end portions 94 and 96, whereas spacer portion 98 communicates directly only with end portion or coil 94. The end of spacer portion 98 at end portion or coil 96 is closed and is adhesively bonded to end portion or coil 96. An additional elongate tubular bladder member 102 is connected to and communicates with end portion 96. At an end opposite end portion 96, member 102 may be provided with a valve (not shown) and nipple or nub connector (not shown), as discussed above with reference to FIGS. 1 and 2, for connection to an irrigation or pressurization tube (not shown). Saline solution or other pressurizing fluid is delivered to retractor 90, e.g., via member 102, for purposes of expanding the retractor from a collapsed insertion configuration (not shown) to the expanded use configuration shown in FIGS. 6 and 7. Member 102 may be additionally connected to and communicate with end portion 94. Member 102 may be additionally connected to and communicate with end portion 94.

Retractor balloon 90 is preferably manufactured from a single elongate tubular preform (not separately illustrated) which is differentially bent and provided with a "memory" to form the coil-shaped end portions 94 and 96 and spacer portions 98, 100, and 102. Spacer portion 102 is a terminal segment of the elongate tubular preform and retains the linear shape thereof. A portion of the elongate tubular preform on one side of linear spacer portion 102 is wound to form end portion or coil 96. On the other side of coil 96, the elongate tubular preform retains its linear shape to form spacer portion 100. On a side of spacer portion 100 opposite coil 96, the elongate tubular preform is wound to form end portion or coil 94. On the other side of coil 94, the elongate tubular preform retains its straight shape to form spacer portion 98. The end of spacer portion 98 is glued to coil 96, while the individual windings of end portions or coils 94 and 96 are adhesively bonded to one another. Accordingly, the balloon retractor 90 is formed from an elongate tubular preform by bending and winding the preform to form the configuration of FIGS. 6 and 7. The balloon has a single linear flow path for the introduction of a pressurizing fluid. In other words, liquid flows in a single path from an inlet to an end of the balloon tube to effectuate an enlargement of the balloon retractor into the expanded configuration. The single path includes, in sequence, spacer tube 102, end coil 96, spacer tube 100, end coil 94, and spacer tube 98. Balloon 90 has a single smooth and continuous wall free of seams.

Figure 8D:
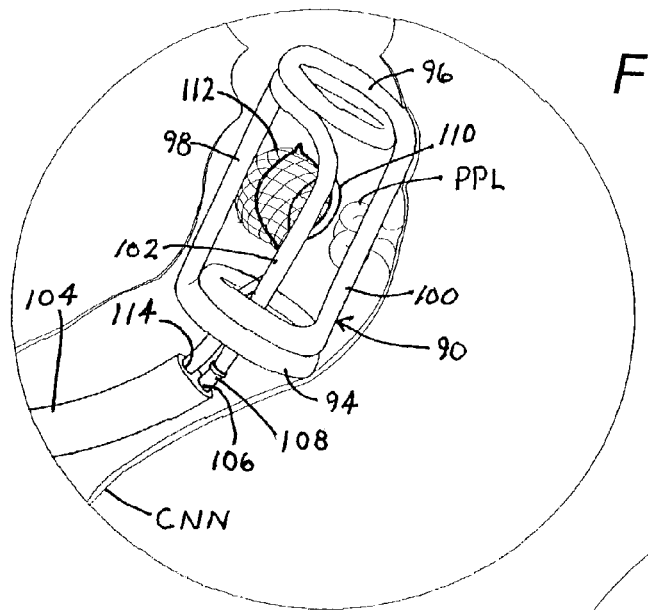
Figure 8E:
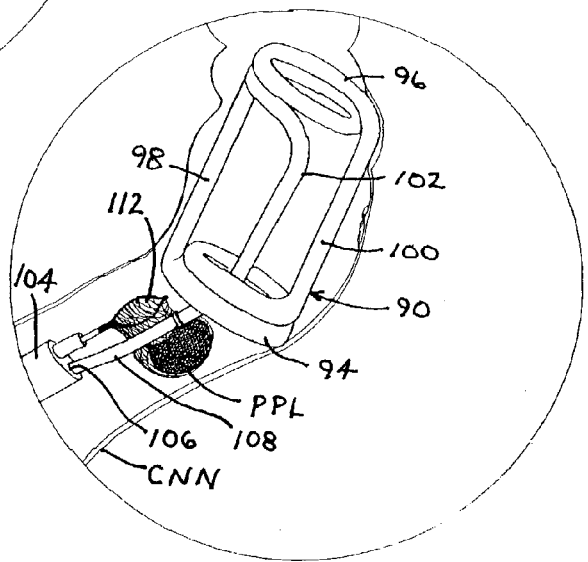
Figure 8F:
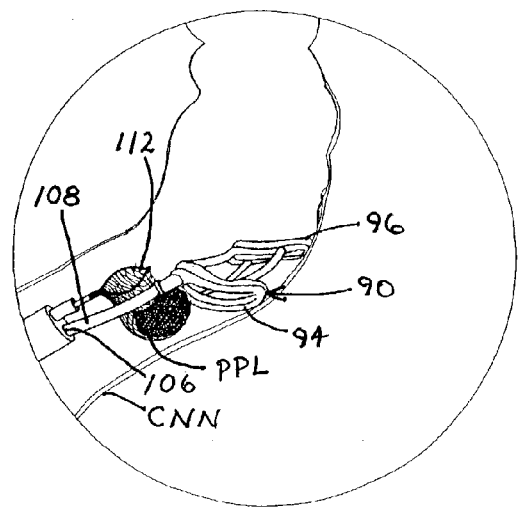

Balloon-type retractor 90 may be used in the same manner as balloon or bladder 16. FIG. 8A shows an endoscope insertion member or shaft 104 that has been inserted into a colon CNN of a human patient. Endoscope insertion member 104 has a biopsy channel 106 (FIG. 8C et seq.) through which retractor balloon 90 (FIGS. 6 and 7) is passed in a collapsed configuration. Retractor balloon 90 is ejected from a distal end of biopsy channel 106 upon the detection, via the endoscope's optical components (not designated), of a polyp PPL. FIG. 8A shows retractor balloon 90 upon an ejection thereof. As shown in FIGS. 8B and 19C, tubular bladder member 102 of retractor balloon 90 is connected to an inflation tube 108 that extends back through biopsy channel 106. A pressurizing fluid such as a saline solution is fed through inflation tube 108 to expand retractor balloon 90. FIG. 8B shows retractor balloon 90 in a partially expanded configuration, while FIG. 8C shows the balloon in a fully expanded configuration that is maneuvered by the endoscopist to straddle polyp PPL. Upon the straddling of polyp PPL, a cauterization snare 110 and capture pocket 112 (see U.S. Pat. Nos. 5,201,740, 5,190,542, 5,741,271 and published International Appln. No. PCT/US02/00840) are ejected from a second biopsy channel 114 of endoscope insertion member 104, as depicted in FIG. 8D. The polyp PPL is severed by the cauterization snare 110 and captured by pocket 112, as shown in FIG. 8E. Retractor balloon 90 is subsequently depressurized, as shown in FIG. 8F and withdrawn from colon CNN, together with endoscope insertion member 104, snare 110, and capture pocket 112, as well as the severed polyp PPL. As shown in FIGS. 8C-8E, the expanded configuration of retractor balloon 90 retracts tissues of colon CNN located ahead of a distal tip of endoscope member 104. thereby facilitating visualization. Inflation tube 108 is connected to retractor balloon 90 and enables use of the retractor balloon in conjunction with endoscope 104 member.

Although the invention has been described in terms of particular embodiments and applications, one of ordinary skill in the art, in light of this teaching, can generate additional embodiments and modifications without departing from the spirit of or exceeding the scope of the claimed invention. For instance, retractor balloon 16 may be formed with a single spacer element such as a cylindrical section instead of a plurality of inflatable spacer rods 30. Another embodiment of a retractor instrument for use in flexible endoscopy such as colonoseopy is a chain of substantially rigid cylindrical parts connected to each other in an expandable cylindrical configuration by pivoting links. The pivoting links may be connected to a screw actuator. Like the embodiment of FIGS. 3 and 4, this embodiment would be mounted to the outer surface of the flexible endoscope insertion member. Typically, the retractor is separable from the insertion member inside the patient, to facilitate the further manipulation of the endoscope. However, as discussed above with reference to FIGS. 3 and 4, two such linkage-type retractor instrument may be mounted to the endoscope insertion member with one of the instruments longitudinally fixed to the endoscope and the other instrument detached and spaced at a variable distance.

Membrane 38 may be omitted in cases where retractor balloon 16 is used as a stiffener for a tortuous colon. In such cases, the endoscope insertion member 14 is manipulated, after the deployment of retractor balloon 16, to traverse opening 32 and aperture 36 during the passage of insertion member 14 to a located further upstream in the patient's colon CLN.

It is to be noted that the retractor instrument and associated methodology disclosed herein may be used with laparoscopes and other rigid endoscopes, as well as with flexible endoscopes. Thus, the term "endoscope insertion shaft" or "endoscope insertion member" as used herein refers to any type of endoscope, whether flexible such as a colonoscope or rigid such as a laparoscope.

The word "endoscopic" as in the term "endoscopic insertion member" is used more broadly herein to denote any type of instrument part inserted into a patient in a minimally invasive surgical procedure involving a flexible or rigid endoscope. For example, an endoscopic insertion member may be a laparoscopic forceps insertable through a trocar sleeve or cannula into a patient for use in a laparoscopic procedure. A balloon retractor in accordance with the invention may be attached about the distal end of the forceps for spreading tissues to facilitate use of the forceps.

The word "spiral" or "spiraling" is used herein to denote a configuration of an elongate member wherein than member is wound about an axis. A coil is a spiral where successive turns are in close juxtaposition or adjacent to one another.

Accordingly, it is to be understood that the drawings and descriptions herein are proffered by way of example to facilitate comprehension of the invention and should not be construed to limit the scope thereof

What is claimed is:

1. An endoscopic retractor instrument comprising a balloon having an inflated or expanded configuration with longitudinally spaced end portions in the form of spiraling tubular coils, said coils being connected to one another by a plurality of mutually transversely spaced elongate spacer tubes, said coils and said spacer tubes being formed from a single bent and wound elongate tubular preform.

2. The retractor instrument defined in claim 1 wherein said tubular coils each have between 1 and 2 windings.

3. The retractor instrument defined in claim 2 wherein tubular coils each have approximately one-and-a-half windings.

4. The retractor instrument defined in claim 1 wherein balloon defines a single pathway for movement of an inflation fluid to inflate said balloon, said single pathway including both of said coils and all of said spacer tubes.

5. The retractor instrument defined in claim 4 wherein said single pathway follows, in sequence, a first one of said spacer tubes, a first one of said coils, a second one of said spacer tubes, a second one of said coils, and a third one of said spacer tubes.

6. The retractor instrument defined in claim 5 wherein said third one of said spacer tubes is connected to said second one of said coils by adhesive.

7. The retractor instrument defined in claim 1 wherein said balloon includes means for deploying said balloon from a distal end of an endoscope.

8. The retractor instrument defined in claim 7 wherein said balloon is insertable in a deflated configuration inside a working channel of the endoscope.

9. The retractor instrument defined in claim 1 wherein said balloon has a single smooth and continuous wall free of seams.

10. An endoscopic retractor comprising a single elongate tubular balloon having an inflated or expanded configuration that is partially spirally coiled to form a cage, said balloon having a single smooth and continuous wall free of seams, said inflated or expanded configuration including a pair of longitudinally spaced coils at opposite ends, said coils being coupled to one another by a plurality of elongate transversely spaced spacer tubes.

11. The retractor defined in claim 10 wherein balloon defines a single pathway for movement of an inflation fluid to inflate said balloon, said single pathway including both of said coils and all of said spacer tubes.

12. The retractor instrument defined in claim 11 wherein said single pathway follows, in sequence, a first one of said spacer tubes, a first one of said coils, a second one of said spacer tubes, a second one of said coils, and a third one of said spacer tubes.

13. The retractor instrument defined in claim 12 wherein said third one of said spacer tubes is connected to said second one of said coils by adhesive.

14. The retractor instrument defined in claim 10 wherein said tubular coils each have between 1 and 2 windings.

15. The retractor instrument defined in claim 10 wherein tubular coils each have approximately one-and-a-half windings.

16. A medical instrument comprising:
a retractor in the form of a balloon having an inflated or expanded configuration with longitudinal spaced end portions in the form of spiraling tubular coils, said coils being connected to one another by a plurality of mutually transversely spaced elongate spacer tubes, said coils and said spacer tubes being formed from a single bent and wound elongate tubular preform; and
means for using said retractor in conjunction with a flexible endoscopic instrument so that an expanded configuration of said retractor retracts tissues located ahead of a distal tip of said endoscopic instrument to facilitate visualization.

17. The retractor instrument defined in claim 16 wherein said tubular coils each have between 1 and 2 windings.

18. The retractor instrument defined in claim 16 wherein balloon defines a single pathway for movement of an inflation fluid to inflate said balloon, said single pathway including both of said coils and all of said spacer tubes.

19. The instrument defined in claim 16 wherein said means for using includes means for attaching said retractor at least indirectly to said endoscopic instrument.

\* \* \* \* \*